(12) United States Patent
Baltzer et al.

(10) Patent No.: US 7,569,661 B2
(45) Date of Patent: Aug. 4, 2009

(54) POLYPEPTIDE SCAFFOLDS AND USE THEREOF

(75) Inventors: Lars Baltzer, Göteborg (SE); Gunnar Dolphin, Linköping (SE); Bo Liedberg, Linköping (SE); Ingemar Lundström, Linköping (SE)

(73) Assignee: Modpro AB, Upsala (SE)

( * ) Notice: Subject to any disclaimer, the term of this patent is extended or adjusted under 35 U.S.C. 154(b) by 299 days.

(21) Appl. No.: 10/512,295

(22) PCT Filed: Mar. 26, 2003

(86) PCT No.: PCT/SE03/00507

§ 371 (c)(1),
(2), (4) Date: May 31, 2005

(87) PCT Pub. No.: WO03/080653

PCT Pub. Date: Oct. 2, 2003

(65) Prior Publication Data

US 2005/0245727 A1    Nov. 3, 2005

(30) Foreign Application Priority Data

Mar. 26, 2002  (SE) .................................. 0200968

(51) Int. Cl.
*A61K 38/00*        (2006.01)

(52) U.S. Cl. ...................................................... 530/324
(58) Field of Classification Search ....................... None
See application file for complete search history.

(56) References Cited

FOREIGN PATENT DOCUMENTS

| WO | 01/85756 A2 | 11/2001 |
|---|---|---|
| WO | 01/85906 A2 | 11/2001 |
| WO | WO 01/85756 A2 * | 11/2001 |

* cited by examiner

*Primary Examiner*—Cecilia Tsang
*Assistant Examiner*—Thomas S Heard
(74) *Attorney, Agent, or Firm*—Merchant & Gould P.C.

(57) ABSTRACT

Novel peptide having a sequence according to SEQ. ID. No. 1, SEQ. ID. No. 2 and/or SEQ. ID. No. 3 are disclosed and also polypeptide scaffold consisting of a four helix bundle formed of two dimerized helix-loop-helix motifs, said helix-loop-helix motifs having sequences according to SEQ. ID. No. 1, SEQ. ID. No. 2 and/or SEQ. ID. No. 3 which may comprise a fluorescent probe at the side chain of Lys15 and a ligand with affinity for a target molecule at the side chain of Lys8 or Lys34.

Also disclosed are polypeptide scaffolds for use in biosensing applications with or without the polypeptide scaffold anchored to a solid surface.

12 Claims, 10 Drawing Sheets

KE2:

```
     1                   15        19
     N-A-A-D-L-E-A-A-I-R-H-L-A-E-K-L-A-A-R
                                        20
                                        -G-P-V-D
                   34                   24
     G-A-R-A-F-A-E-F-K-K-A-L-Q-E-A-L-Q-A-A
     42
```

KE3:

```
     1                   15        19
     N-A-A-D-L-E-A-K-I-R-H-L-A-E-K-L-A-A-R
                                     20  23
                                        -G-P-C-D
                                        24
     G-A-R-A-F-A-E-F-R-R-A-L-Q-E-A-L-Q-A-A
     42
```

LA-42b:

```
     1                        19
     N-A-A-D-Nle-E-A-A-I-K-H-L-A-E-K-Nle-A-A-K
                                        20
                                        -G-P-V-D
                                        24
     G-A-R-A-F-A-E-F-Orn-K-A-L-Q-E-A-Nle-Q-A-A
     42
```

*Fig. 6*

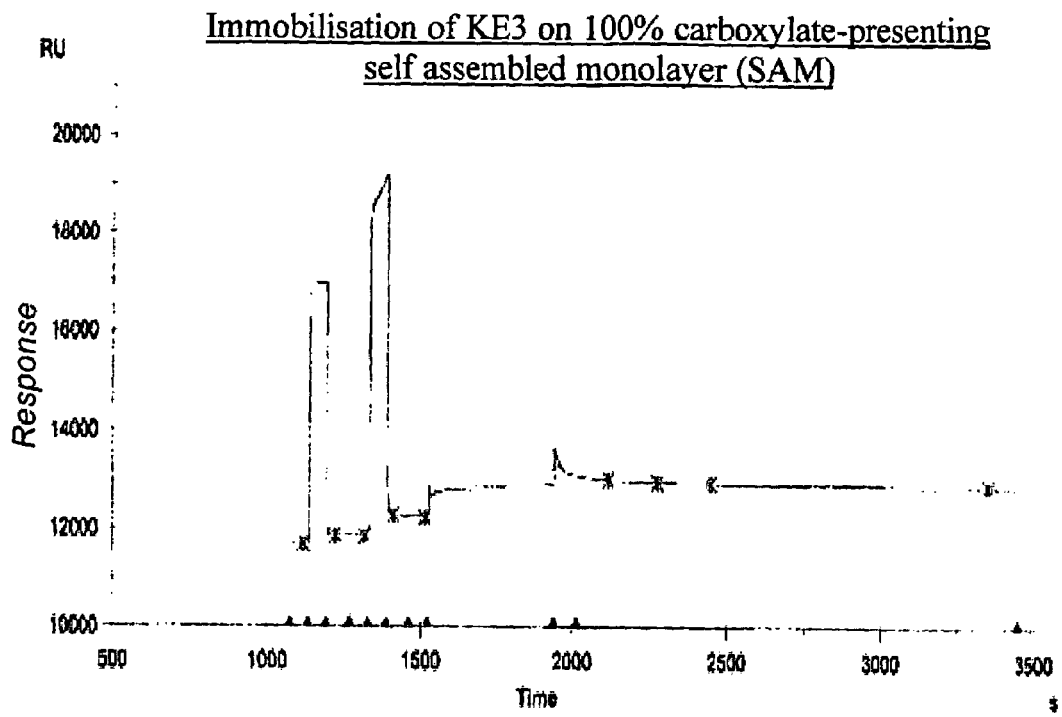
| Fc | Time | AbsResp | Slope | Baseline | RelResp | Id |
|---|---|---|---|---|---|---|
| 1 | 1115.5 | 11693.8 | 0.02 | Yes | 0 | |
| 1 | 1218.5 | 11864.8 | -0.07 | No | 171.0 | aktivering EDC/NHS |
| 1 | 1312.5 | 11858.9 | -0.09 | Yes | 165.1 | |
| 1 | 1408.5 | 12287.4 | -2.00 | No | 426.5 | derivalisering PDEA |
| 1 | 1512.5 | 12242.6 | -0.06 | Yes | 383.7 | |
| 1 | 2117.5 | 13020.6 | -0.45 | No | 776.0 | 40 uM KE3 i fosfat pH 6.0 |
| 1 | 2275.5 | 12975.6 | -0.20 | No | 733.0 | |
| 1 | 2445.5 | 12951.3 | -0.12 | No | 706.7 | |
| 1 | 3349.5 | 12901.2 | -0.01 | No | 658.6 | |
activation 1 min
coupling of PDEA 1 min
coupling of KE3 7 min
[KE3] = 40μM in 10 mM phosphate buffer pH 6.0
Level of immobilisation: >600 RU
1 RU⇔1 pg/mm$^2$
If dimension of folded peptide is 20x20 Å$^2$, ~20-30 % of surface is covered by KE3
*Fig. 9, cont.*

POLYPEPTIDE SCAFFOLDS AND USE THEREOF

FIELD OF THE INVENTION

The present invention relates to novel polypeptide scaffolds and use thereof.

BACKGROUND OF THE INVENTION

The de novo design of folded polypeptides aims at improving our understanding of protein structure, and also provides a platform for the engineering of new proteins with tailored functions [DeGrado, W. F.; Summa, C. M.; Pavone, V.; Nastri, F.; Lombardi, A. *Annu. Rev. Biochem.* 1999, 68, 779-819; Micklatcher, C.; Chmielewski, J. *Curr. Opin. Chem. Biol.* 1999, 3, 724-729; Baltzer, L.; Nilsson, H.; Nilsson, J. *Chem. Rev,* 101, 3153-3164. Designed, folded polypeptides that undergo pH-controlled, site selective self-functionalization with ligands [Broo, K.; Brive, L.; Lundh, A. C.; Ahlberg, P.; Baltzer, L. *J. Am. Chem. Soc.* 1996, 118, 8172-8173; Baltzer, L.; Nilsson, J. *Curr. Opin. Biotechnol.* 2001, 12, 355-360] constitute an excellent toolbox for the construction of various complex molecular systems, e. g. model glycoproteins [Andersson, L.; Stenhagen, G.; Baltzer, L. *J. Org. Chem.* 1998, 63, 1366-1367; Andersson, L. K.; Dolphin, G. T.; Kihlberg, J.; Baltzer, L. *J. Chem. Soc.-Perkin Trans.* 2 2000, 459-464] or complex receptors.

SUMMARY OF THE INVENTION

The object of the present invention is to provide folded, ligand modified helix-loop-helix polypeptide scaffolds that connect the key biosensing events of recognition and reporting. The well characterized interaction between the enzyme human carbonic anhydrase II, HCAII, and its inhibitor 4-carboxybenzenesulfonamide [Vidgren, J.; Svensson, A.; Liljas, A. *Int. J. Biol. Macromol.* 1993, 15, 97-100] (Ia) was selected for a proof of principle demonstration. However, the variety of molecules that can be incorporated, and the ease by which their relative positions can be varied, allow for functional units for a wide range of receptor-ligand systems to be systematically developed.

More precisely, the present invention relates to novel peptides having a sequence according to SEQ. ID. No. 1, SEQ. ID. No. 2 and/or SEQ. ID. No. 3. These peptides constitute helix-loop-helix motifs. The helix-loop-helix motif having SEQ. ID. No. 2 is shown as KE2 in FIG. 6, and the helix-loop-helix motif having SEQ. ID. No. 3 is shown as KE3 in FIG. 6.

The invention also relates to polypeptide scaffold consisting of a four helix bundle formed of two helix-loop-helix motifs, i.e. two of the above mentioned peptides, which have dimerized.

Furthermore, the invention relates to the use the above mentioned polypeptide scaffolds in bioanalytical/biosensor applications.

Finally, the invention relates to the use of such polypeptide scaffolds in biosensors for determination of protein concentrations and/or protein affinities.

The characterizing features of the invention will be evident from the following description and the appended claims.

DETAILED DESCRIPTION OF THE INVENTION

Preferred polypeptide scaffold according to the invention are SEQ. ID. No 1, KE2 (SEQ. ID. No. 2) and KE3 (SEQ. ID. No. 3) bound to a polypeptide sequence that makes them form a helix-loop-helix motif. Thus KE2 may dimerize with a second copy of KE2 to form a four-helix bundle, and KE3 may dimerize with a second copy of KE3 to form a four-helix bundle. KE2 may also dimerize with KE3, to form a heterodimer or with SEQ. ID. No 1 or another sequence based on that of KE2 or KE3, and that have the same hydrophobic residues in the same positions in the sequence and form the helix-loop-helix motif.

The polypeptide scaffold according to the invention preferably comprises a ligand with affinity for a target molecule or ion. By "target molecule or ion" is intended a molecule or ion to which said ligand binds for the purpose of detection and quantification. For example, if the polypeptide scaffold has been functionalized with a ligand that specifically binds a metal ion the purpose is to detect and quantify that "target" metal ion. If the polypeptide scaffold has been functionalized with a ligand with high specificity for a protein the purpose is to identify and quantify that "target" protein. Targets include, but are not limited to metal ions and proteins. Interesting target molecules are, e.g., biomolecules. Preferably said ligand is localized at the side chain of a lysine residue. In KE2 this lysine residue preferably is Lys34 because it is preferentially acylated due to its low pKa value and in KE3 this lysine residue is Lys8 because it is close to the His residue in position 11 which ensures the site selectivity. The choice of the ligand depends on the intended use of the polypeptide scaffold. For detection of enzymes the ligand is chosen from their known inhibitors, for detection of proteins other than enzymes, that have high affinity ligands, the ligand to be attached to the scaffold is chosen from the known ligands of the protein. For carbohydrate binding proteins the ligand is a carbohydrate. For DNA and RNA the ligand is DNA, RNA or PNA. For target proteins for which there are no known ligands, the ligands to be attached to the scaffold are several compounds from a combinatorial library. One example of such a ligand is benzenesulfonamide which is an inhibitor of carbonic anhydrase II. Any thrombin inhibitor can be used for the detection of thrombin and protease inhibitors can be used for the detection of proteases. For detection of ions the ligand is an ion binding functionality or chelating group.

The polypeptide scaffold according to the invention preferably also comprises a reporter group, or reporting group, for enabling detection of the binding to the ligand. Identification and quantification of a target ion is for example of interest in the study of environmental pollution or in process control. Identification and quantification of biomolecules such as metabolites or proteins are of interest in the diagnosis and treatment of disease. The reporter group can e.g. be a fluorescent probe. This fluorescent probe may be e.g. dansyl, fluorescein, rhodamine or Oregon Green derivatives. Preferably it is attached to the side chain of Lys15. The positions of the ligand and the fluorescent probe may be reversed in each polypeptide.

The ligand and the reporter group may either both be attached to the same polypeptide chain or be attached to different polypeptide chains of the dimer.

Two or more polypeptide scaffolds may be arranged e.g. in the form of an array on a biosensor chip or in the wells of a microtiter plate. When a microtiter plate is used, the polypeptide scaffolds may be present in a solution or in a polymeric hydrogel in the wells of the plate. It may also be possible to use a solution in indentations, pits or cavities on the chip or in the wells of the microtiter plate. The chip can be made of metal, insulator, semiconductor or polymer. The chip can also consist of a thin coating of the above mentioned materials, e.g. in the form of an array, on top of a supporting substrate.

It is often preferable to immobilize the polypeptide scaffolds on the surface of e.g. a chip, a microtiter plate, a vesicle, a micelle, or a membrane. Examples of such surfaces are artificial surfaces such as modified or unmodified surfaces of a metal, an insulator, a semiconductor or a polymer. Other examples of surfaces to which the polypeptide scaffoldes may be immobilized are surfaces of vesicles, micelles and membranes. It may be preferable to include an anchoring group in the polypeptide scaffold according to the invention. One way of doing this is to introduce an amino acid with a high affinity for the surface onto which the polypeptide scaffolds are to be immobilized, such as a chip or microtiter plate or a vesicle or membrane. One example of doing this is to introduce at position 22 of the loop region a Cys, Lys or Glu residue or a non-natural amino acid. The site of introduction is not limited to position 22, but may be any position in the loop region in positions 20-24 of the sequence. The non-natural amino acid may e.g. have an aminooxy function. Another way is to attach a bifunctional linker molecule to an amino acid residue in the polypeptide. Preferably, the anchoring group has been introduced site-specifically into the polypeptide scaffold by attachment of a bifunctional molecule to an amino acid residue specifically introduced to react chemoselectively or site-selectively with the bifunctional linker molecule according to the principles described above. The introduced amino acid or linker molecule should be able to form a strong chemical bond to the surface onto which the polypeptide scaffolds are to be immobilized, such as a chip or microtiter plate or a vesicle or membrane, and they could be of the type —SH, COOH, $NH_2$, biotin, his-tag, fatty acid, cholesterol etc. The bifunctional molecule may have the general structure X—$R_n$—Y, wherein X is a functional group of the type COOH, $NH_2$, SH, SSAr, CHO, $CH_2Br$, $CH_2Cl$, or $CH_2I$, $R_n$ is an alkyl or ethylene glycol chain comprising n carbons, and Y is a group of the type COOH, $NH_2$, SH, biotin, biotin analogue, His-tag, fatty acid or cholesterol.

The binding of the polypeptide scaffold can occur either directly to the substrate surface onto which the polypeptide scaffolds are to be immobilized, such as a chip or microtiter plate or a vesicle or membrane, or indirectly via a surface modification formed on the surface onto which the polypeptide scaffolds are to be immobilized, such as a chip or microfiter plate or a vesicle or membrane. The surface modification can be a self-assembled monolayer, a protein layer (e.g. streptavidin), a polymer network, a hydrogel, a His-tag etc.

A cysteine residue introduced into the polypeptide scaffold can react via the SH group directly with the surface, e.g. gold. A cysteine residue introduced in the same way also can react via the SH group with a disulphide attached to the surface, FIG. 9. This latter procedure is only meant as an illustration and is explained in FIG. 8, but many other methods exist which will achieve the same purpose.

The polypeptide scaffold according to the invention is highly suitable for determination of protein concentrations and protein affinities in biosensing applications. It can also be used for the determination of DNA, RNA and PNA concentrations and affinities, as well as carbohydrate concentrations and affinities.

In the determination of protein concentrations or affinities polypeptide scaffolds may be used in arrays where the ligands of the polypeptide scaffolds have the same or different affinities for the protein or other substance that is to be studied.

When polypeptide scaffolds having different affinities are used in arrays for biosensing applications they are suitable for measurements of analyte concentrations, and when polypeptide scaffolds having the same affinity are used in arrays for biosensing applications they are suitable for measurements of the affinity of the analyte for the ligand used through the use of different dilutions of the sample for the different spots of the array. It is for example of interest to be able to determine the concentrations of proteins that are related to a disease, and to be able to determine the affinities of those proteins. Altered concentrations and affinities may suggest a pathological condition or the absence of a pathological condition. It is also of interest to be able to monitor the concentrations and affinities of proteins to prevent disease, and to predict the probability of disease. It is also of interest to determine the concentration of m-RNA, or carbohydrates or other biomolecules.

The invention will now be further explained in the following example. The example is only intended to illustrate the invention and should in no way be considered to limit the scope of the invention.

BRIEF DESCRIPTION OF THE DRAWINGS

In the examples, reference is made to the accompanying drawings on which:

FIG. 6 shows the sequences of KE2 and KE3, and also of LA-42b.

EXAMPLE

Figure 1:
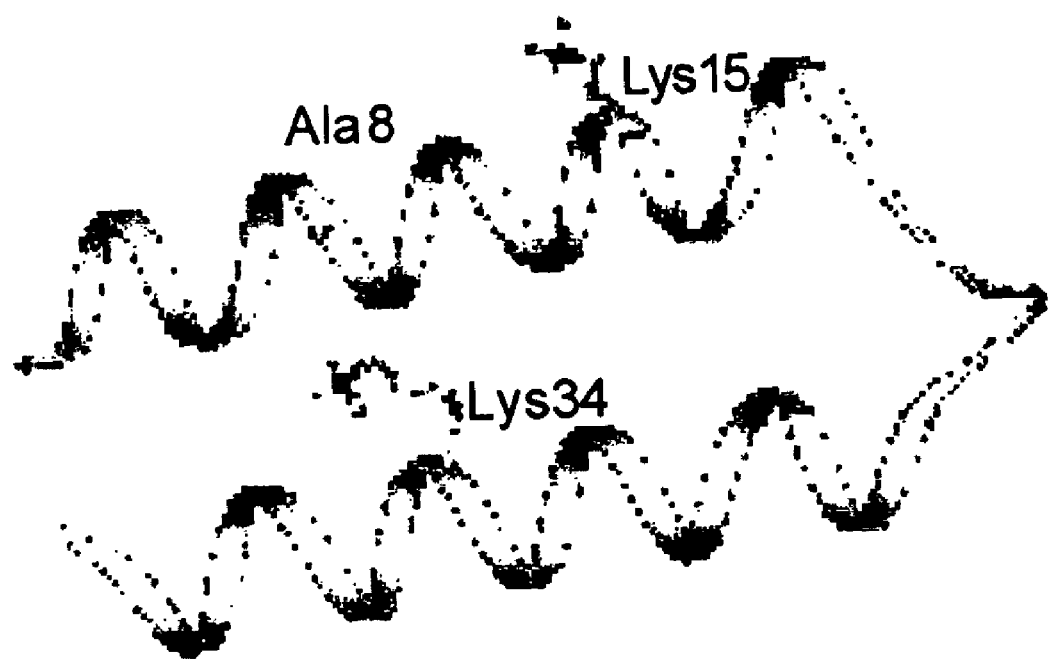
FIG. 1 shows a modeled structure of KE2 and KE3, showing sites of introduction of dansyl, position 15, and benzenesulfonamide, positions 34 and 8, respectively. Only the amino acid side chains in positions involved in functionalization are shown and only those in the sequence of KE2. Amino acid sequences of KE2 and KE3, where lysine residues in bold represent sites of modification, are also shown.

The design of the polypeptides KE2 and KE3 (see FIG. 1) was based on the sequence of LA-42b, a 42 residue polypeptide that folds into a helix-loop-helix motif and dimerizes to form a four helix bundle [Andersson, L.; Stenhagen, G.; Baltzer, L. *J. Org. Chem.* 1998, 63, 1366-1367] (shown in FIG. 6 and as SEQ. ID. No. 4). Out of 42 residues of LA-42b more than 32 were conserved in the design of KE2 and KE3. The solution structure of LA-42b has been extensively studied by NMR and CD spectroscopy and because of the sequence similarities with KE2 and KE3 they, too, were assumed to fold into helix-loop-helix dimer motifs in aqueous solution. They were synthesized using solid phase peptide synthesis and identified by mass spectrometry. The MALDI-TOF spectra of KE2 and KE3 showed single peaks at 4446.3 and 4563.2, respectively (calc. 4446.0 and 4563.2). The peptides were designed to allow the site-specific incorporation of a fluorescent probe at the side chain of Lys 15, as well as of a ligand with high affinity for a target protein at the side chains of Lys34 (KE2) or Lys8 (KE3). The side chain of Lys15 was orthogonally protected to allow the coupling of a fluorescent probe on the solid-phase. Before cleaving the peptide from the resin the Lys15 Alloc protection group was removed by three equivalents of Pd $(PPh_3)_4$ in a mixture of 9.25 mL $CHCl_3$, 0.5 mL AcOH and 0.5 mL N-methylmorpholine. Reaction of the selectively deprotected peptides with two equivalents of dansyl chloride in the presence of eight equivalents of diisopropylethylamine in DMF provided KE2-P and KE3-P. The MALDI-TOF spectra of KE2-P and KE3-P showed single peaks at 4680.4 and 4868.2, respectively (calc. 4679.4 and 4867.6). The notation –P indicates that a fluorescent probe has been covalently attached and the notation –PL indicates the attachment of both fluorescent probe and high-affinity ligand.

The incorporation of the benzenesulfonamide ligand was accomplished by reacting the polypeptides with the active ester Id in aqueous solution at pH 8. One of the inventors et al have previously shown that Lys34 is the most reactive of all lysine residues in LA-42b [Andersson, L. K.; Caspersson, M.; Baltzer, L. Chem. Eur J. 2002, In press] in terms of its reactivity towards active esters, because it is situated in a position that forms a part of the hydrophobic core, and has a selectively depressed $pK_a$ value. Some competition from Lys19 was observed [Andersson, L. K.; Dolphin, G. T.; Baltzer, L. ChemBio-Chem, 2002, in press] and therefore Lys19 was replaced by Arg19 in the sequence of KE2, and so was Lys10. No competition from Lys33 was expected based on the previous investigation and it was therefore not removed. In KE3 Lys8 is less reactive than Lys34 and Lys19, and only equally reactive as Lys10 and Lys33, and consequently in KE3 all competing lysines were replaced by Arg residues.

The affinity of HCAII for unprotonated Ia in aqueous phosphate buffer at room temperature and pH 6.5 has been reported previously, and the equilibrium dissociation constant $K_d$ was 27 µM. [Taylor, P. W.; King, R. W.; Burgen, A. S. V. *Biochemistry* 1970, 9, 2638-2645] Preliminary surface plasmon resonance-based affinity measurements suggested that $K_d$ for KE2-PL modified with Ib was in the µM range and the inventors reasoned that in order to avoid competition from non-specific binding of HCAII a higher affinity ligand than that corresponding to Ia was needed. With benzenesulfonamide derivatives bearing alkyl chains of different lengths in the para position, increased affinities towards HCAII as compared to that of Ia have been reported [King, R. W.; Burgen, A. S. V. *Proc. R. Soc. Lond. B* 1976, 193, 107-125]. Thus, to increase the affinity of the benzenesulfonamide inhibitor, and to minimize sterical constraints upon HCAII binding that could be introduced by coupling the benzenesulfonamide ligand to the peptide, an aliphatic spacer was introduced. The N-hydroxysuccinimidyl ester of 4-carboxybenzenesulfonamide (Ib) was reacted with 6-aminohexanoic acid to form Ic, which was further activated with N-hydroxysuccinimide to form Id. 1.4 equivalents of Id were allowed to react with 1 equivalent of KE2-P or KE3-P in 50 mM Tris-HCl buffer at pH 8.0 and room temperature. The modified peptides KE2-PL and KE3-PL were purified by reversed-phase HPLC on a Hichrom C-8-column using 0.1% TFA in 40% aqueous 2-propanol as the eluent and lyophilized. The yield was 55% and 77% for KE2-PL and KE3-PL, respectively. The MALDI-TOF spectra of KE2-PL and KE3-PL showed single peaks at 4977.2 and 5165.0, respectively (calc. 4975.7 and 5163.9).

Figure 2:
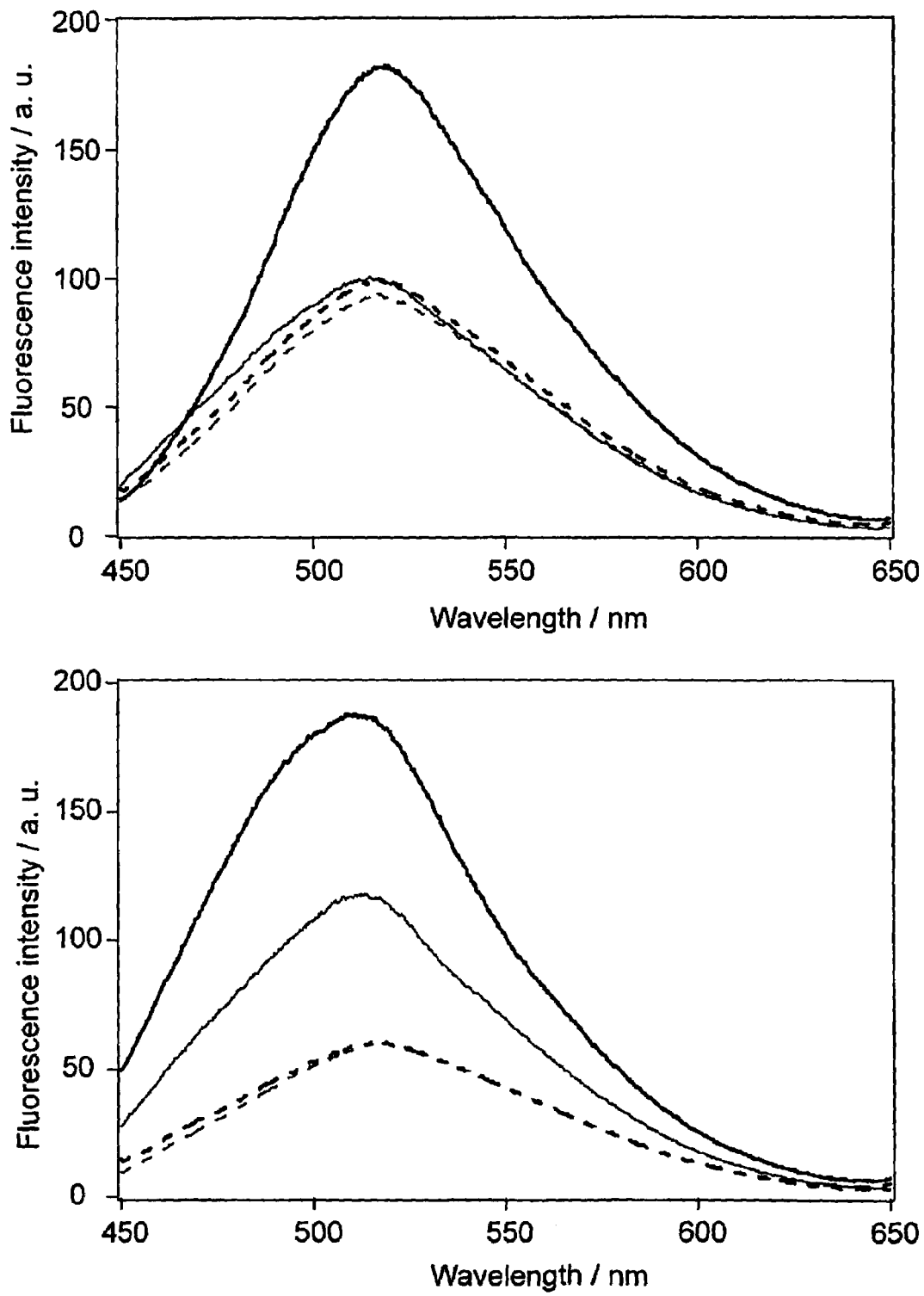
FIG. 2 shows a fluorescence spectrum of 1 µM KE2 (upper) and KE3 (lower) modified with the dansyl fluorescent probe. Bold and thin curves correspond to peptides with and without benzenesulfonamide, respectively (KE2-PL, KE3-PL and KE2-P, KE3-P). Dotted lines represent spectra in the absence of HCAII, solid lines represent spectra where 50 µM HCAII has been added. The fluorescence of the control peptides KE2-P and KE3-P is not affected by the presence of HCAII, but the fluorescence of KE2-PL is increased by 80%. KE3-PL displays a similar, but less pronounced, behavior. Note the significant difference between the fluorescence of KE3-PL and KE3-P.

The biosensing capabilities of KE2-PL and KE3-PL were investigated by recording their fluorescence emission spectra between 450 and 650 nm upon excitation at 335 nm. Spectra were recorded of 1 µM peptide solutions in 10 mM HBS buffer at pH 7.4 and 298 K, in the absence and presence of 50 µM HCAII, with 1 µM solutions of KE2-P and KE3-P as negative controls, FIG. 2. Upon addition of HCAII, the fluorescence intensities of KE2-PL and KE3-PL increased by 80% and 60%, respectively, whereas the fluorescence intensities of the control peptides were not affected by HCAII. The observed intensity increases were thus caused by the binding of HCAII to the benzenesulfonamide moiety of the peptide scaffolds, with negligible effects induced by non-specific protein-peptide interactions. The inventors interpret the intensity increases to arise from a change in molecular environment of the dansyl group upon binding of HCAII by the polypeptides; it appears that the probe is partially quenched in the unbound peptide, but less so when bound to HCAII. The polypeptides KE2-PL and KE3-PL are therefore capable of reporting on the presence of the target protein HCAII. Recognition is ensured by the specificity of the benzenesulfonamide ligand.

Figure 3:
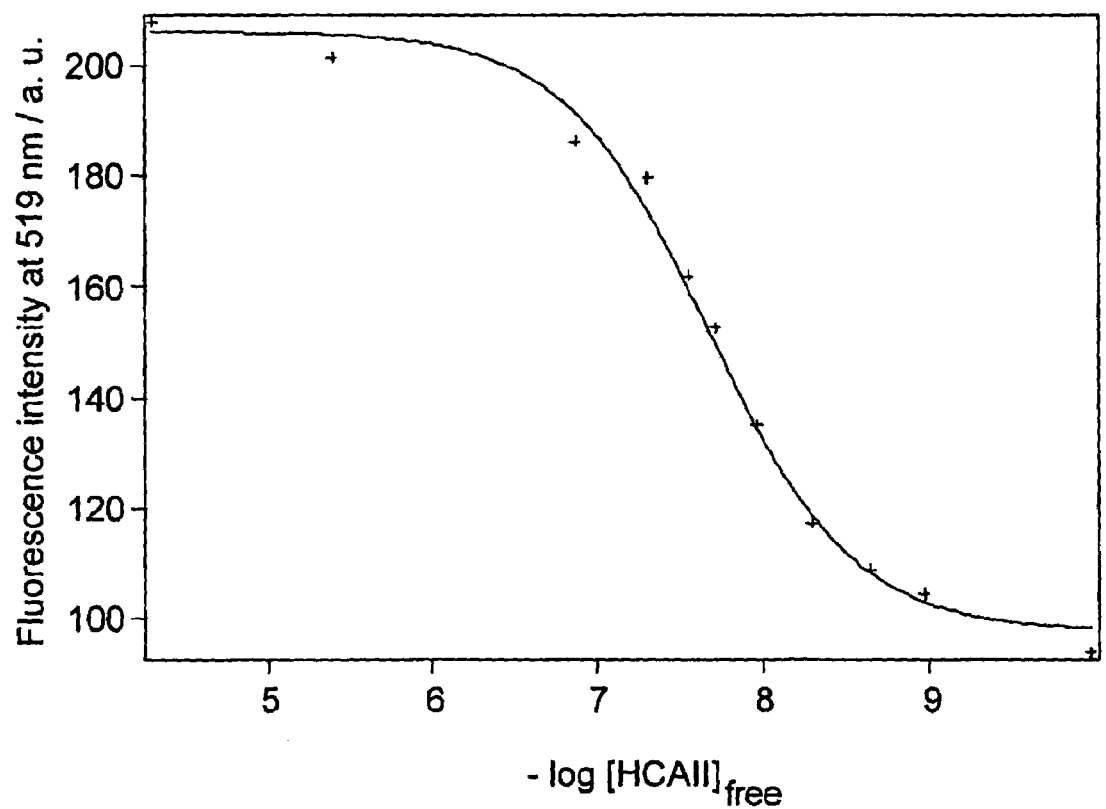
FIG. 3 shows a sigmoid binding curve obtained upon titration of 1 µM KE2-PL with HCAII by plotting the maximum fluorescence intensity versus the logarithm of free HCAII concentration. The affinity of the interaction was estimated to be 0.02 µM from curve fitting using a two-state binding model.

Upon titration of 1 µM KE2-PL with 5 nM-50 µM HCAII, a sigmoid curve was obtained, FIG. 3. For the bimolecular association between KE2-PL and HCAII, the equilibrium dissociation constant $K_d$ equals the concentration of free HCAII at the inflexion point. $K_d$ was estimated to be 0.02 µM from the best fit to the experimental results of an equation describing the dissociation of a bimolecular complex. This result constitutes the proof of principle for functional helix-loop-helix-based biosensor units, since binding results in fluorescence intensity changes. The use of an array of peptides modified with ligands of different affinities, makes measurements of analyte concentrations possible, at levels of accuracy limited, in principle, only by the number of different ligand variants available, and by the affinity range of those variants.

The CD spectra of 1 µM solutions of KE2-P and KE3-P in 10 mM phosphate buffer at pH 7.5 revealed a higher degree of helical content than that of the template peptide LA-42b at comparable concentrations [Andersson, L. K.; Dolphin, G. T.; Kihlberg, J.; Baltzer, L. *J. Chem. Soc.-Perkin Trans.* 2

Figure 4:
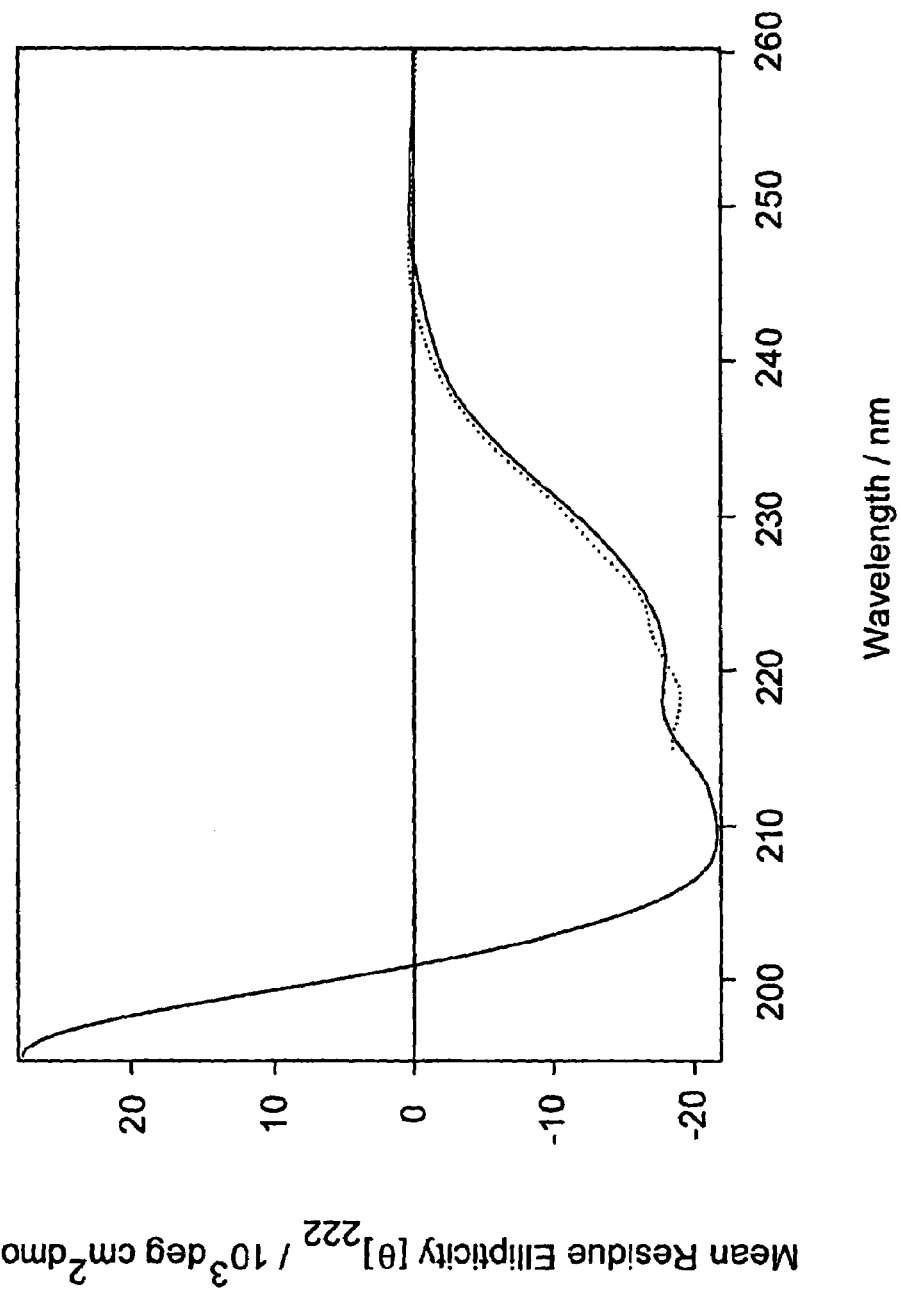
FIG. 4 shows mean residue ellipticity of 1 µM KE2-PL (solid curve) and 1 µM KE2-PL in the presence of 2 µM HCAII (dotted curve). The dotted curve is the difference spectrum obtained by subtracting the spectrum of 2 µM HCAII from that of 1 µM KE2-PL+2 µM HCAII. The spectrum of KE2-PL shows two minima at 208 and 222 nm that are typical of α-helical proteins. The helicity of the peptide was retained upon binding to HCAII.
Figure 5:
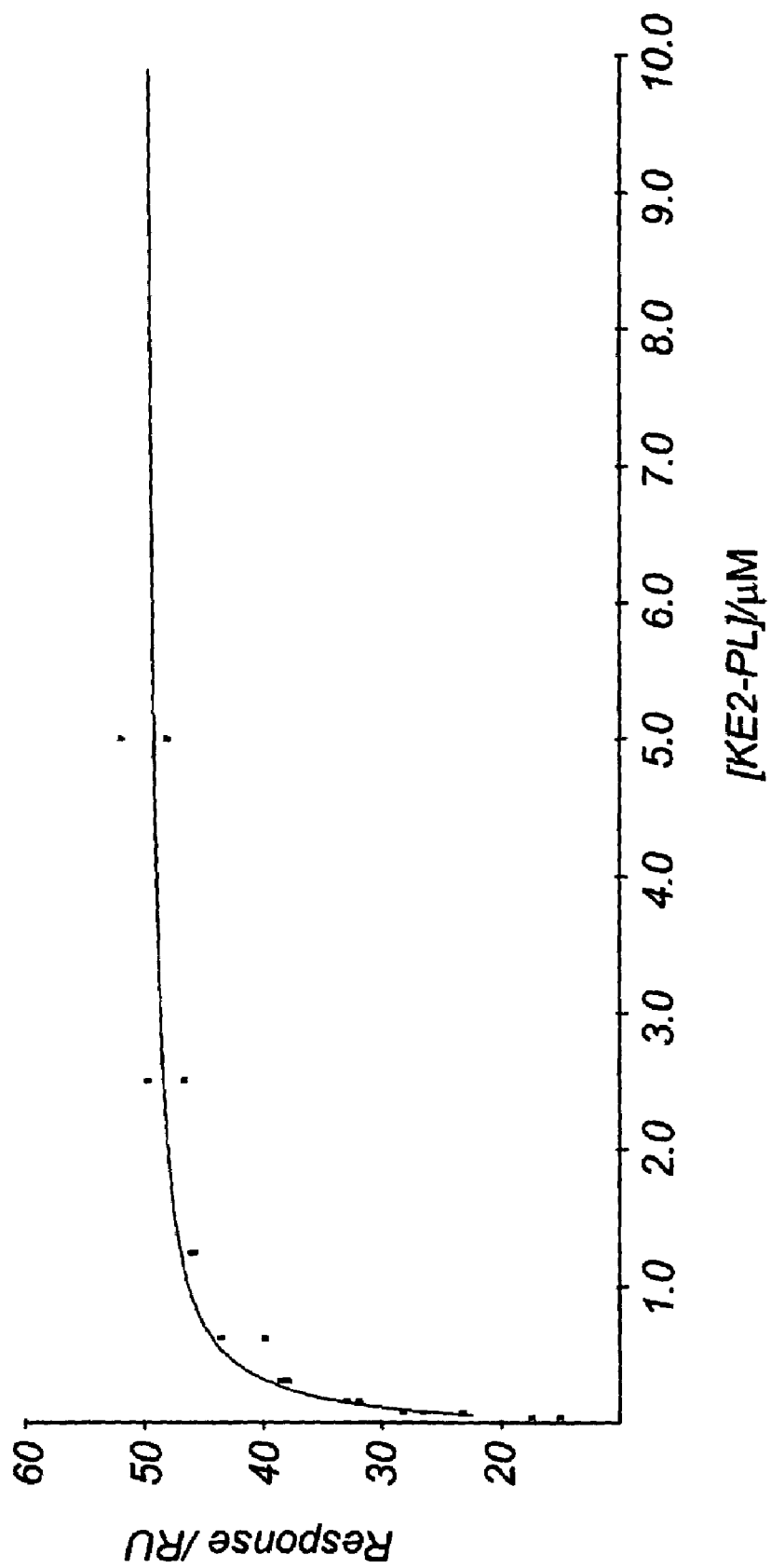
FIG. 5 shows the affinity of the interaction between KE2-PL and HCAII was estimated to be 0.08 µM from a surface plasmon resonance-based analysis. The solid line represents the theoretical curve for equilibrium response as a function of peptide concentration with $K_d$=0.08 µM (bimolecular interaction model). Experimental data from duplicate measurements are shown.
Figure 7:
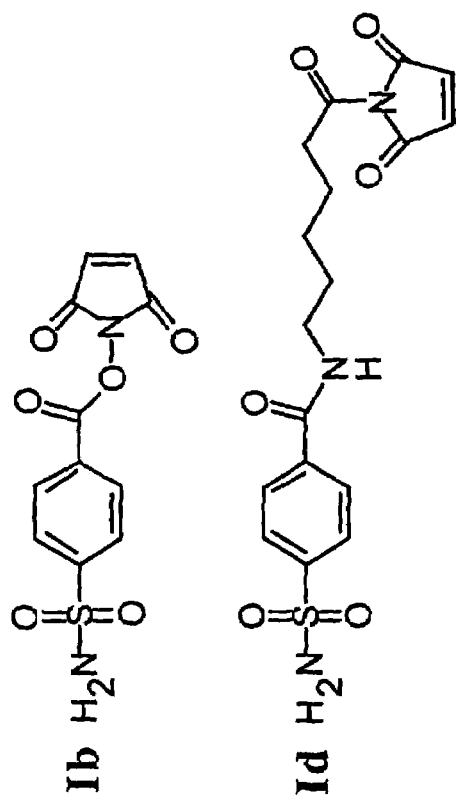
FIG. 7 shows the structures of compounds Ia, Ib, Ic and Id.
Figure 7:
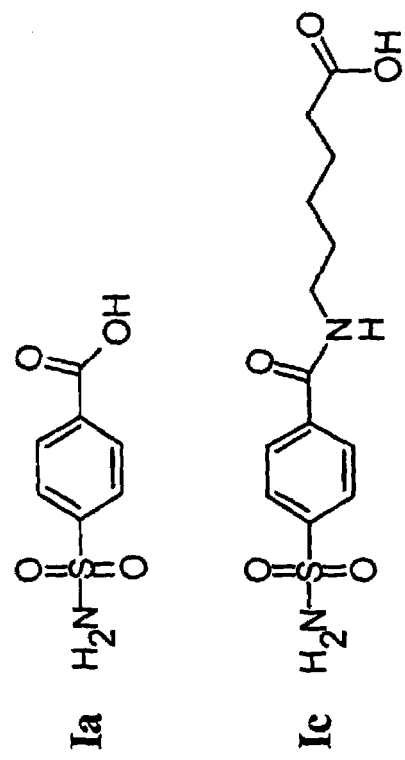
Figure 8:
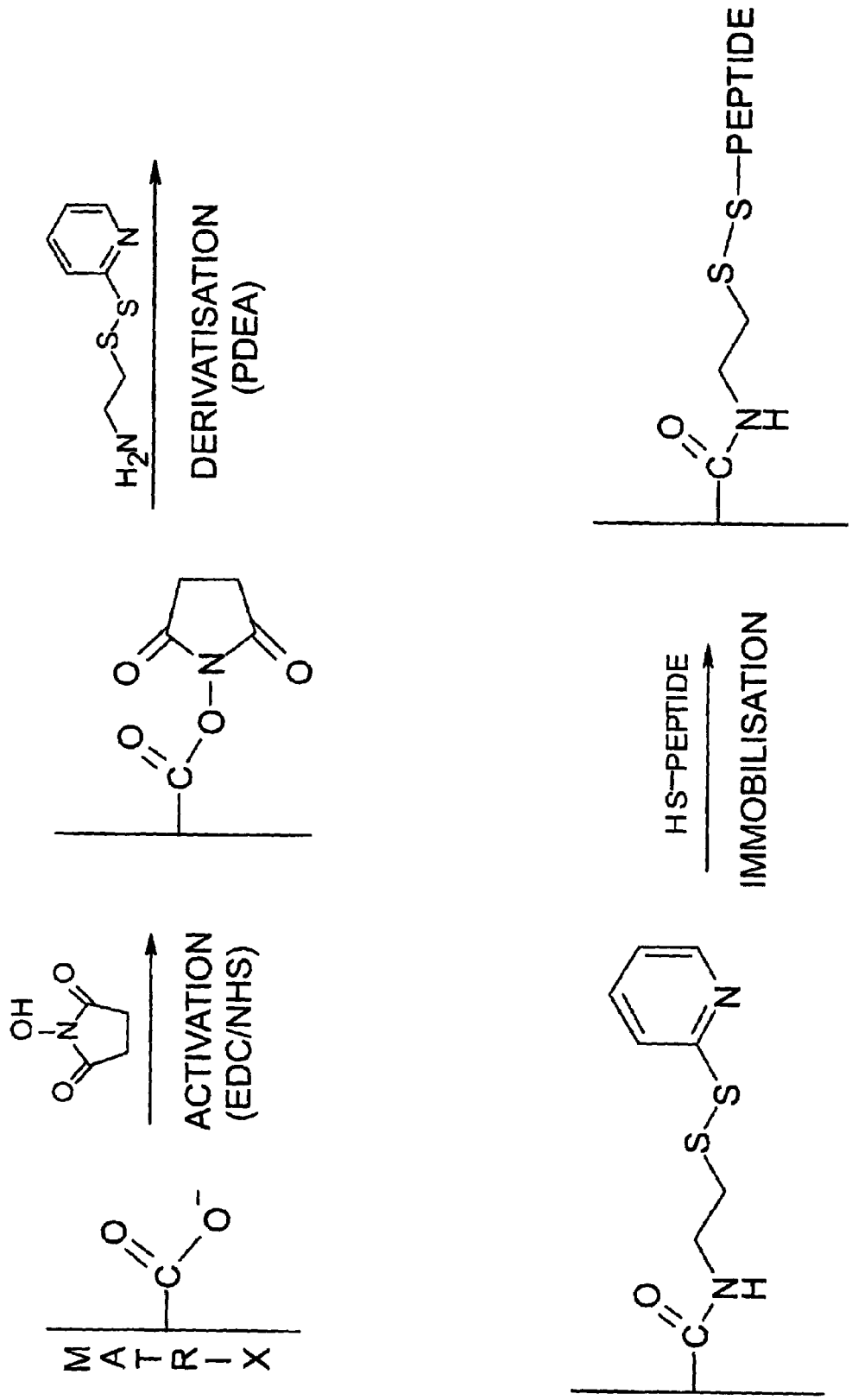
FIG. 8 illustrates the procedure of immobilization via PDEA where a carboxylate residue linked to the gold surface of a Biacore chip is transformed into an N-hydroxysuccinimide (NHS) ester using EDC as coupling agent, and reacted with PDEA to form the corresponding amide. The Cys residue of the peptide KE3 was then reacted with the PDEA moiety to form the covalent disulfide bond.
Figure 9:
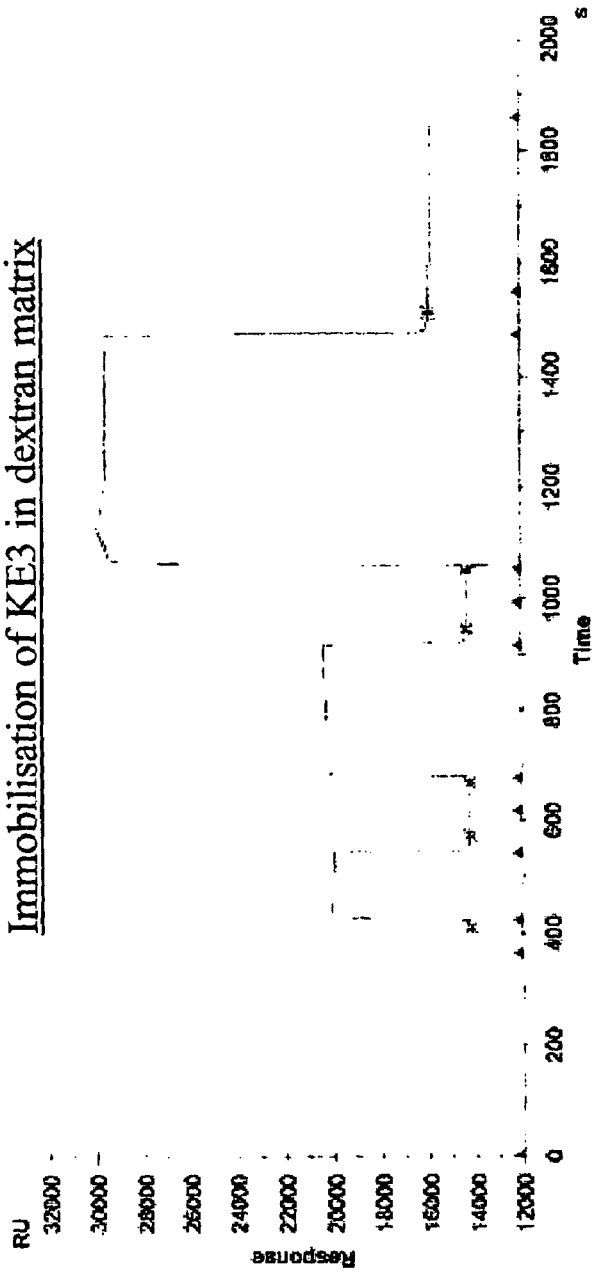
FIG. 9 shows a Biacore sensorgram describing the immobilization of KE3 in dextran matrix and on 100% carboxylate-presenting self assembled monolayer (SAM)using the procedure of FIG. 8.

2000, 459-464]. The mean residue ellipticity $\theta_{222}$ was −18 200 and −15 900 deg cm$^2$ dmol$^{-1}$ for 1 µM KE2-P and KE3-P, respectively, and that of 3 µM LA-42b was −7 500 deg cm$^2$ dmol$^{-1}$. The large difference between the KE-P peptides and LA-42b suggests that the probe has an effect on helix stability, possibly due to the removal of a positive charge upon probe attachment [Andersson, L. K.; Dolphin, G. T.; Kihlberg, J.; Baltzer, L. *J. Chem. Soc.-Perkin Trans.* 2 2000, 459-464] or due to interactions between the probe and the hydrophobic core. Difference CD spectra obtained by subtracting that of 2 µM HCAII from that of 1 µM KE2-PL and 2 µM HCAII showed that the helicity of KE2-PL was unchanged upon binding to HCAII, FIG. 4. At these concentrations, and based on a dissociation constant of 0.02 µM, more than 90% of the peptide is bound to HCAII.

There was a significant difference between the fluorescence intensities of KE3-P and KE3-PL in the absence of HCAII. The attachment of a ligand in position 8 close to the probe in position 15 may change the peptide structure enough to decrease the quenching. This hypothesis is supported by the observed differences in helical contents between 1 µM KE3-P and 1 µM KE3-PL, $\theta_{222}$=−15 900 and −21 300 deg cm$^2$ dmol$^{-1}$, respectively.

The affinity obtained from fluorescence spectroscopy was compared to that measured with a surface plasmon resonance-based method, where the interaction between immobilized HCAII and KE2-PL in solution was monitored for a series of peptide concentrations ranging from 40 nM to 10 µM. The steady state affinity was estimated to be 0.08 µM from curve fitting to a plot of equilibrium responses as a function of peptide concentration using a 1:1 binding model. Slightly non-ideal behavior was observed, which might be explained by an influence on the affinity by concentration-dependent supersecondary structure formation of the peptide. The steady-state affinity of HCAII for Ic was also determined and $K_d$ was found to be 0.044 µM. The results suggest that the affinity of HCAII for the ligand decreases due to steric effects when the ligand is attached to the peptide. An even longer spacer might be useful to increase the affinity of HCAII for the peptide even further.

It has been shown that components that have been designed to specifically recognize and bind an analyte and to signal this event via a reporter group can be introduced in a small synthetic molecule as part of a chemosensor. [Czarnik, A. W. *Chem. Biol.* 1995, 2, 423-428; Chen, C. T.; Wagner, H.; Still, W. C. *Science* 1998, 279, 851-853]. In a biosensor, the recognition event is based on a biochemical mechanism, involving e.g. antibodies, enzymes or whole cells [Thevenot, D. R.; Toth, K.; Durst, R. A.; Wilson, G. S. *Pure Appl. Chem.* 1999, 71, 2333-2348]. The polypeptide scaffolds according to the invention have been designed and synthesized and as they are further modified with ligands their functions resemble those of chemosensors. However, as the scaffolds themselves do not contribute to recognition, which is based on a bio-chemical mechanism, the inventors present the ligand-modified polypeptides, with or without a reporter group, according to the inventions as functional units in biosensor systems.

These results demonstrate the first steps in the successful application of folded helix-loop-helix peptides to the area of biosensing. A peptide that binds to a receptor has been shown to be able to report on this event via a fluorescent probe. Furthermore, this concept has been applied to the determination of an affinity constant. The possibility of conveniently incorporating a wide range of probes and ligands at different relative positions provides an attractive way of optimizing the biosensing conditions, such as sensitivity and response, for any target biomacromolecule. As indicated by these results, the structure of the peptide scaffold also plays an important role in sensor performance. A determination of analyte concentration is possible using an array of peptides modified with ligands of different affinities.

The invention claimed is:

1. Polypeptide having a sequence according to SEQ. ID. No. 1, SEQ. ID. No. 2 and/or SEQ. ID. No. 3.

2. Polypeptide consisting of a four helix bundle formed of two dimerized helix-loop-helix motifs, said helix-loop-helix motifs having sequences independently selected from SEQ. ID. No. 1, SEQ. ID. No. 2 and SEQ. ID. No. 3.

3. Polypeptide according to claim 2 comprising in one or both of the polypeptide chains of the dimerized helix-loop-helix motifs, a ligand with affinity for a target molecule or ion, and a reporter group which gives use to a measurable signal upon binding of said ligand to said target molecule or ion.

4. Polypeptide according to claim 3 wherein said target molecule is a biomolecule.

5. Polypeptide according to claim 4 wherein said ligand is selected from the group consisting of peptides with affinity for a protein, proteins with affinity for a protein, inhibitors of an enzyme, agonists of a receptor protein, antagonists of a receptor protein, parts of DNA, parts of RNA, parts of PNA, carbohydrates, haptens, toxins, metabolites, hormones, ion chelating agents, drugs, steroids, lipids and combinations of two or more of such ligands.

6. Polypeptide according to claim 3, wherein said reporter group is at attached to the side chain of Lys15.

7. Polypeptide according to claim 3, wherein said reporter group is a fluorescent probe.

8. Polypeptide according to claim 7, wherein said fluorescent probe is selected from the group consisting of dansyl, fluorescein, and rhodamin.

9. Polypeptide according to claim 2 wherein both dimerized helix-loop-helix motifs have SEQ. ID. No. 2.

10. Polypeptide according to claim 2 wherein both dimerized helix-loop-helix motifs have SEQ. ID. No. 3.

11. Polypeptide according to claim 3 comprising at least one helix-loop-helix motif having SEQ. ID. No. 2, wherein said ligand with high affinity for a target molecule or ion is attached the side chain of Lys34 in said at least one helix-loop-helix motif having SEQ. ID. No. 2.

12. Polypeptide according to claim 3, comprising at least one helix-loop-helix motif having SEQ. ID. No. 3, wherein said ligand with high affinity for a target molecule or ion is attached to the side chain of Lya8.

* * * * *

SEQUENCE LISTING

```
<160> NUMBER OF SEQ ID NOS: 4

<210> SEQ ID NO 1
<211> LENGTH: 42
<212> TYPE: PRT
<213> ORGANISM: Artificial Sequence
<220> FEATURE:
<223> OTHER INFORMATION: General Peptide
<220> FEATURE:
<221> NAME/KEY: MISC_FEATURE
<222> LOCATION: (8)..(8)
<223> OTHER INFORMATION: variable
<220> FEATURE:
<221> NAME/KEY: MISC_FEATURE
<222> LOCATION: (22)..(22)
<223> OTHER INFORMATION: variable
<220> FEATURE:
<221> NAME/KEY: MISC_FEATURE
<222> LOCATION: (33)..(34)
<223> OTHER INFORMATION: variable

<400> SEQUENCE: 1

Asn Ala Ala Asp Leu Glu Ala Xaa Ile Arg His Leu Ala Glu Lys Leu
1               5                   10                  15

Ala Ala Arg Gly Pro Xaa Asp Ala Ala Gln Leu Ala Glu Gln Leu Ala
            20                  25                  30

Xaa Xaa Phe Glu Ala Phe Ala Arg Ala Gly
            35                  40
```

```
<210> SEQ ID NO 2
<211> LENGTH: 42
<212> TYPE: PRT
<213> ORGANISM: Artificial Sequence
<220> FEATURE:
<223> OTHER INFORMATION: Synthetic Peptide KE2

<400> SEQUENCE: 2

Asn Ala Ala Asp Leu Glu Ala Ala Ile Arg His Leu Ala Glu Lys Leu
1               5                   10                  15

Ala Ala Arg Gly Pro Val Asp Ala Ala Gln Leu Ala Glu Gln Leu Ala
            20                  25                  30

Lys Lys Phe Glu Ala Phe Ala Arg Ala Gly
            35                  40

<210> SEQ ID NO 3
<211> LENGTH: 42
<212> TYPE: PRT
<213> ORGANISM: Artificial Sequence
<220> FEATURE:
<223> OTHER INFORMATION: Synthetic Peptide KE3

<400> SEQUENCE: 3

Asn Ala Ala Asp Leu Glu Ala Lys Ile Arg His Leu Ala Glu Lys Leu
1               5                   10                  15

Ala Ala Arg Gly Pro Cys Asp Ala Ala Gln Leu Ala Glu Gln Leu Ala
            20                  25                  30

Arg Arg Phe Glu Ala Phe Ala Arg Ala Gly
            35                  40

<210> SEQ ID NO 4
<211> LENGTH: 42
<212> TYPE: PRT
<213> ORGANISM: Artificial Sequence
<220> FEATURE:
<223> OTHER INFORMATION: Synthetic Template Peptide LA-42b
<220> FEATURE:
<221> NAME/KEY: MISC_FEATURE
<222> LOCATION: (5)..(5)
<223> OTHER INFORMATION: Nle
<220> FEATURE:
<221> NAME/KEY: MISC_FEATURE
<222> LOCATION: (16)..(16)
<223> OTHER INFORMATION: Nle
<220> FEATURE:
<221> NAME/KEY: MISC_FEATURE
<222> LOCATION: (27)..(27)
<223> OTHER INFORMATION: Nle
<220> FEATURE:
<221> NAME/KEY: MISC_FEATURE
<222> LOCATION: (34)..(34)
<223> OTHER INFORMATION: Orn

<400> SEQUENCE: 4

Asn Ala Ala Asp Xaa Glu Ala Ala Ile Lys His Leu Ala Glu Lys Xaa
1               5                   10                  15

Ala Ala Lys Gly Pro Val Asp Ala Ala Gln Xaa Ala Glu Gln Leu Ala
            20                  25                  30

Lys Xaa Phe Glu Ala Phe Ala Arg Ala Gly
            35                  40
```